United States Patent
Jameson (12)

(10) Patent No.: US 6,384,086 B1
(45) Date of Patent: May 7, 2002

(54) ETHENE CONTAINING SOLUTIONS AND USE THEREOF IN METHODS OF THERAPY OR PROPHYLAXIS

(76) Inventor: Warwick Murrow Jameson, 135 Gloaming Hill, Titahi Bay, Porirua, Wellington (NZ)

( * ) Notice: Subject to any disclaimer, the term of this patent is extended or adjusted under 35 U.S.C. 154(b) by 0 days.

(21) Appl. No.: 09/190,165

(22) Filed: Nov. 12, 1998

Related U.S. Application Data

(63) Continuation-in-part of application No. PCT/NZ97/00059, filed on May 14, 1997.

(30) Foreign Application Priority Data

May 14, 1996 (NZ) ................................................ 286571

(51) Int. Cl.[7] .............................................. A61K 31/02
(52) U.S. Cl. ..................................................... 514/762
(58) Field of Search ................................. 514/762, 885; 99/323.1

(56) References Cited

U.S. PATENT DOCUMENTS

| | | |
|---|---|---|
| 3,557,529 A | 1/1971 | Ranke |
| 4,692,179 A | 9/1987 | Mehra |
| 5,220,097 A | 6/1993 | Lam et al. |

FOREIGN PATENT DOCUMENTS

| | | | |
|---|---|---|---|
| WO | WO8912794 | | 12/1989 |
| WO | WO9317081 | | 9/1993 |
| WO | WO9400551 | | 1/1994 |
| WO | WO94/00551 | * | 1/1994 |
| WO | WO95/17214 | | 6/1995 |
| WO | WO9517214 | | 6/1995 |

OTHER PUBLICATIONS

International Agency for Research on Cancer: Monographs of . . . , vol. 60, 1994, Ethylene, as published by World Health Org.

* cited by examiner

*Primary Examiner*—Marianne C. Seidel
*Assistant Examiner*—Donna Jagoe
(74) *Attorney, Agent, or Firm*—Jacobson Holman, PLLC

(57) ABSTRACT

The present invention provides ethene containing solutions and the use thereof in methods of therapy and prophylaxis. Specifically provided are storage stable solutions comprising ethene solubilized in a suitable liquid. Methods of therapy and prophylaxis contemplated include direct and indirect action against disease and microorganisms, as well as methods for improving metabolic function and priming or causing a host to mount a protective response against disease or microorganisms.

13 Claims, 2 Drawing Sheets

ETHENE CONTAINING SOLUTIONS AND USE THEREOF IN METHODS OF THERAPY OR PROPHYLAXIS

This invention is a continuation-in-part application of PCT/NZ97/00059, filed on May 14, 1997.

TECHNICAL FIELD

This invention relates generally to ethene containing solutions and to the use thereof in methods of therapy or prophylaxis.

BACKGROUND OF THE INVENTION

The current state of the art in respect of the metabolic role of ethene in mammals is best described in International Agency for Research on Cancer: Monographs of the Evaluation of Carcinogenic Risks to Humans Vol 60, 1994, Ethylene, as published by the World Health Organization. From this reference it may be concluded that ethene has no useful metabolic role in mammals (apart from use as an anaesthetic) and that its production or uptake by mammals seems to be without useful metabolic purpose.

The state of the art was advanced in specification PCT/NZ94/00151 (published as WO 95/17214 and for which the present applicant is an inventor) by the suggestion that ethene production by mammals may be a defense mechanism directed against invading micro-organisms. The use of ethene as a novel sterilizing agent was therefore described therein. Particularly described were sterilizing or micro-organism inhibiting solutions comprising ethene solubilized in a suitable liquid.

It was indicated that the solutions of WO 95/17214, would have utility in prophylaxis and/or therapy through a direct antimicrobial effect on infective or disease causing agents.

The application has now identified a disadvantage associated with the use of the solutions of WO 95/17214. These solutions have been found to exhibit poor storage and chemical stability. This lack of stability is believed to result from ethene's ability to react with other components in solutions.

More specifically, the applicant has found that ethene may react with other components in a liquid resulting in one or more of, a reduction in the amount of ethene in solution, alteration in the pH of the solution or the production of undesirable reaction products. The applicant has surprisingly found that ethene in solution may be reduced by 50% for example by reaction with such components. The applicant has found such reactions entirely unanticipated and at variance with the disclosure of WO 95/17214.

These components may comprise ions, for example H+ and OH− ions, calcium ions, or other impurities such as microscopic plant matter, calcium solids, or entrained gases, for example, air, oxygen or chlorine.

While not bound by the following, it is suggested for example, that one reaction may be between hydroxy ions and ethene forming 2-hydroxy ethene. Similarly, oxygen entrained in an ethene containing solution may also react with ultra violet light, or even neon light to produce ozone which subsequently reacts with ethene to produce ethylene oxide. The presence of a carcinogen such as ethylene oxide greatly reduces the utility of the ethene containing liquid for consumption. Moreover, all of these reactions may reduce the amount of ethene solubilized in the liquid.

By way of example, the applicant has found that ethene added to a suitable liquid, in this case water of a potable standard containing components giving a conductivity of 148 micromhos (reciprocal megohms) per centimetre, reacted to give a rise in pH which may continue over days and months of storage. A similar reaction was not observed when the water used was deionised by distillation to substantially zero conductivity prior to the addition of ethene.

A lack of storage stability is particularly disadvantageous for this ethene product if it is to be involved in lengthy transport operations, or where an extended shelf life is desirable.

As noted above, the applicant has now surprisingly found that an ethene containing solution exhibiting usefully increased chemical and storage stability can be produced by solubilizing ethene in a reactivity reduced liquid. The solution produced is useful as a tonic.

It is therefore an object of the invention to provide a storage stable solution comprising ethene solubilized in a suitable liquid or at least to provide the public with a useful choice.

It is a further object of the invention to provide methods of prophylaxis and/or therapy in which the storage stable solution is used as a directly active antimicrobial agent, or again at least to provide the public with a useful choice.

It was also the applicant's expectation that the solutions of WO 95/17214 would have utility in prophylaxis and/or therapy through a direct antimicrobial effect on infective or disease causing agents. However, the applicant has found that ethene containing solutions may not have a direct sterilizing/inhibiting effect against a number of micro-organisms in vitro. Some examples of micro-organisms found by the applicant not to be sterilized in vitro by solubilized ethene are: Influenza A (H3N2), Poliovirus type 1 (Sabin) and Herpes simplex virus. In addition to these viruses, eight bacterial strains representing four bacterial genera (Staphylococcus, Pseudomonas, Klebsiella, Enterococcus) of important human pathogens were tested in vitro without apparent sterilizing success.

The applicant has surprisingly found that, notwithstanding the apparent lack of an in vitro antimicrobial efficacy of ethene on certain micro-organisms, ethene, more particularly solubilized ethene, may provide prophylactic and/or therapeutic effects in vivo in hosts to which the ethene is administered. This is even against a micro-organism such as Herpes simplex which ethene does not inhibit or sterilize in vitro. In other words, an ethene induced micro-organism sterilizing/inhibiting effect may be observed in a host, even though the micro-organism(s) within that host may not be directly ethene labile. In this respect the applicant has found that a useful metabolic role of ethene in man is the same as its useful metabolic role in plants, that of a primary immunogen. It is upon this entirely unexpected finding that this invention is also partly based.

It is therefore a further object of the invention to provide methods of prophylaxis and/or therapy in which ethene is used otherwise than as a directly active antimicrobial agent, or at least to provide the public with a useful choice.

SUMMARY OF THE INVENTION

In a first aspect, the present invention can be said to broadly consist in a storage stable solution comprising ethene solubilized in a suitable liquid. The storage stable solution is preferably a tonic solution comprising ethene solubilized in a reactivity reduced liquid.

Desirably, the liquid is purified. Most preferably, the liquid is a deionized liquid.

In a general aspect, the present invention provides a method for improving metabolic function in a host which method involves administering to the host an effective amount of a storage stable solution of the invention.

In a further aspect, the present invention provides a method for prophylaxis and/or therapy for the treatment of diseases or infections in a host by exerting a direct antimicrobial effect, and which involves the step of administering to the host an effective amount of a storage stable solution of the invention.

In a related aspect, the present invention provides the use of a storage stable solution of the invention in the preparation of a medicament for use in prophylaxis and/or therapy against microbial infection, whereby the medicament exerts a direct antimicrobial effect.

In a still further aspect, the present invention can be said to broadly consist in a method for prophylaxis and/or therapy for the treatment of diseases or infections in a host other than through exerting a direct antimicrobial effect and which involves the step of administering to the host an effective amount of ethene.

More generally, the invention provides a method of improving metabolic function in a host which method involves the step of administering to the host an effective amount of ethene, and provided that the improved metabolic function is achieved other than through exerting a direct antimicrobial effect In a further aspect, the present invention provides a method of priming and/or causing a host to mount a protective response, more particularly a protective immune response, against disease or infective micro-organisms and which involves the step of administering to the host an effective amount of ethene.

In a still further aspect, the invention provides a method of administering ethene to a host wherein the ethene provides an indirect sterilizing or micro-organism inhibiting effect, such effect being prophylactic and/or therapeutic and such effect being caused by host systemic factors, for example, T-lymphocytes, or leukocytes potentiated in the host by the administration of ethene.

In still a further aspect, the present invention may provide a method of therapy and/or prophylaxis against microbial infection in a host which comprises the steps of:

(a) administering an effective amount of ethene to said host to potentiated and/or prime the immune system of the host to generate a host protective immune response against said microbial infection; and (b) administering an amount of an active agent which has a direct antimicrobial effect sufficient to sterilize or at least inhibit the micro-organism.

In the context of this application, the host is preferably human but may be animal.

In one preferred embodiment of the indirect acting methods of the invention, the immune response induced by the administration of ethene is a humoral response.

Conveniently, the administration of ethene causes the production of systemic factors, for example in cases of HIV infection, cells involved in mounting a humoral immune response to be increased.

Most conveniently and by way of example, the administration of ethene may cause the population of CD4 T-lymphocytes to increase, remain stable or decrease at a slower rate than would otherwise be the case without the administration of ethene.

The host protective response engendered through the administration of ethene may also be a healing effect in damaged tissue of the host involved in mounting an immune response, for example liver tissue or lymphatic tissue, and thus enable such tissues to function to better general, metabolic and immunological effect.

In a particularly preferred but not limiting embodiment of the indirect methods, the micro-organism against which the therapeutic effect is to be mounted is HIV. The therapeutic effect may be directed at other micro-organisms as well for example, Herpes simplex, or micro-organisms involved in Hepatitis or Glandular fever infection. More preferably, but not essentially, the therapeutic administration of ethene may be in combination or conjunction with other antimicrobial substances, for example Zidovudine (AZT), or antibiotics such as Penicillin.

In the methods of the invention where ethene is required to be administered for indirect effects it is conveniently provided in the form of a composition containing ethene solubilized in a suitable liquid such as water. Most desirably, ethene is more suitably administered in the form of the storage stable solution of the invention.

In another aspect, the present invention provides the use of ethene in the preparation of a medicament for use in prophylaxis and/or therapy against microbial infection, whereby the medicament induces an indirect antimicrobial effect through an ability to prime and/or cause the host to mount a protective response, particularly a protective immune response, against infection.

The invention is precedingly broadly defined. However, those persons skilled in this art will appreciate that the invention is not limited to only those aspects defined but that it also includes embodiments for which the following description provides examples.

BRIEF DESCRIPTION OF THE DRAWINGS

Further, the present invention will be better understood by reference to the accompanying drawings in which.

DETAILED DESCRIPTION

Figure 1:
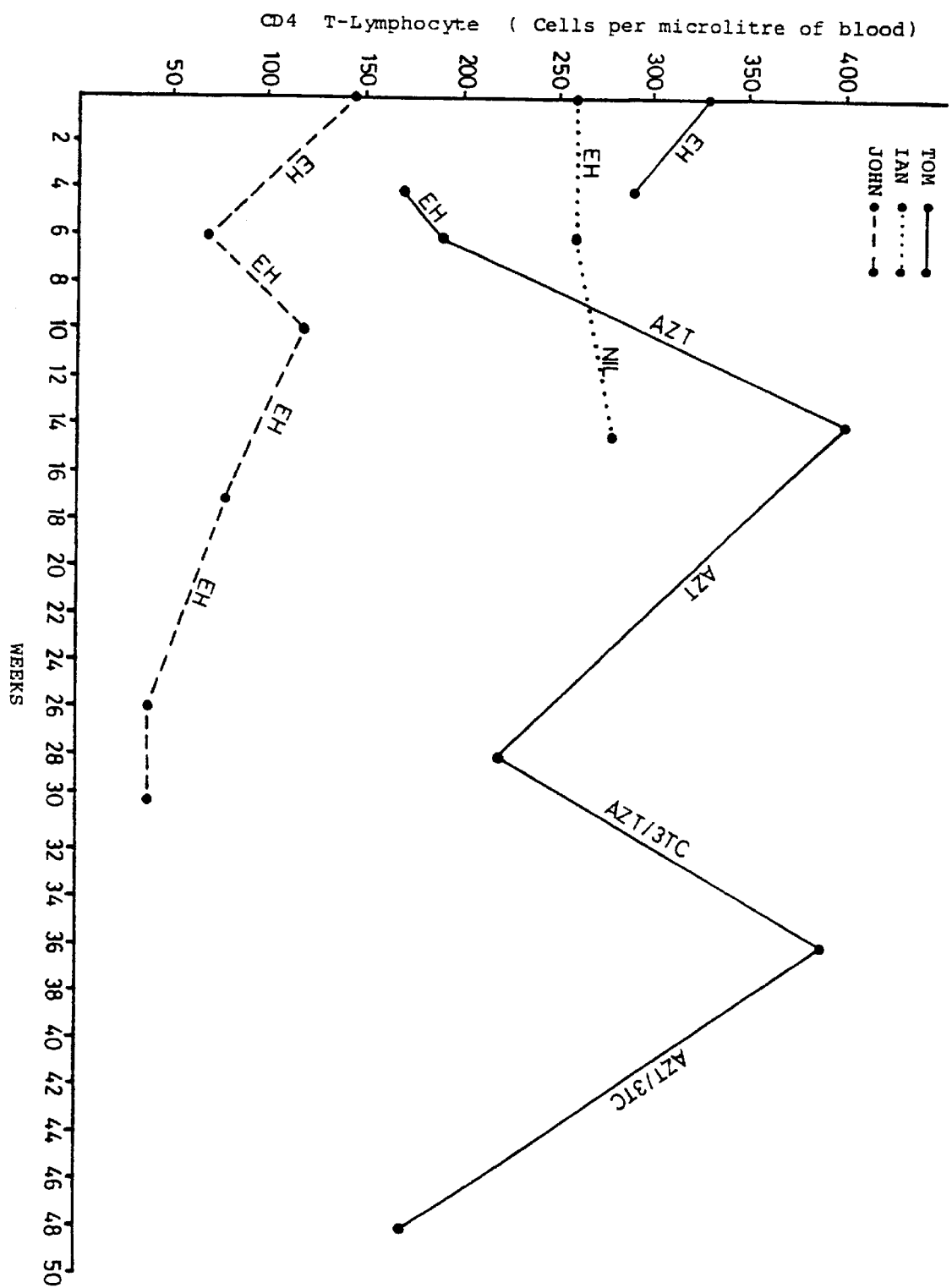
FIG. 1 illustrates the effect of the administration of ethene to individuals infected with HIV/AIDS.

As outlined above, there are a number of findings which underlie the present invention.

The first basic finding is that an ethene containing solution which exhibits enhanced chemical and storage stability can be produced by solubilizing ethene in a suitable liquid.

The second basic finding of the applicant which underlies the present invention is that ethene, more preferably solubilized ethene, as a micro-organism sterilant/inhibitor, may produce a micro-organism sterilizing and/or inhibiting effect in a host even if the particular micro-organism is not directly ethene labile. This is because the applicant has surprisingly found that ethene is capable of inducing a host response, the products of which may have the effect of acting against a disease and/or infective micro-organism in a sterilizing and/or inhibiting manner. Ethene therefore has application in methods of prophylaxis and/or therapy against microorganisms and/or diseases.

By the term "tonic", the applicant means a product which produces a useful metabolic effect (excluding general anaesthesia) in a host animal administered same.

The term "micro-organism" or the like is used herein in a broad sense by the applicant to mean bacterial, viral and fungal disease causing infective agents and their metabolites as well as infective particles such as viral RNA.

By "deionised", in one embodiment the applicant means a liquid part removed of ions or, or liquid having a level of ionisation suitable for use in producing a storage stable solution of the invention. In another embodiment the applicant means a liquid treated to usefully remove or reduce its ion content. Preferably, the ratio of ions present in the treated liquid relative to the same liquid prior to treatment is 5:10, preferably less than 2.5:10 more preferably less than 1:10 and most preferably 3:1,000,000 or lower. For accuracy, ionisation levels are preferably determined in the liquids after removal of any entrained carbonic acid. Ionisation levels are preferably determined as milligrams per litre present in solution, but may be measured in terms of conductivity (micromhos/cm).

The term "disease" is used by the applicant in its classically broad sense of disturbance, including diseases caused by micro-organisms as well as diseases in which no micro-organism is involved such as cancer; injury, ailment, deformity, disorder or adverse condition of body or mind.

The term "impurities" as used by the applicant herein refers to any component in a liquid that reacts with ethene, directly or indirectly, including ions.

By the term "purified", the applicant means in one embodiment a liquid treated to usefully remove entrained impurities whereby up to fifty percent (50%), preferably at least seventy five percent (75%) and most preferably greater than ninety five percent (95%) of the impurities have been removed. In another embodiment, the applicant means a liquid having a relatively high degree of purity (or relatively low level of impurities) which can be used to provide a storage stable solution of the invention.

The term "reactivity reduced liquid" as used in this specification means a liquid that has been purified to an extent that such purification usefully inhibits the rate of decay of ethene added to the liquid. The term also refers to a liquid, the viscosity of which has been increased to a level that usefully impedes the rate of decay of ethene added to the liquid. The term includes a denatured liquid.

Therefore, the first aspect of the present invention lies in a solution comprising ethene solubilized in a suitable liquid which is storage stable. This term will be readily understood by the art skilled worker. In a broad sense it refers to an ethene containing solution wherein the level of ethene remains relatively constant over a period of time. In one embodiment it refers generally to an ethene containing solution with storage stability superior to results previously achieved. In another embodiment it refers to an ethene containing solution wherein the level of ethene does not change significantly over a period of one month. Preferably, a solution wherein there is no significant change in ethene levels over six months, and more preferably over twelve months.

The liquid employed in the solution may be any liquid suitable for providing the requisite storage stability. This may include any liquids with levels of conductivity, purification, or ionisation which can be used to provide a storage stable solution of the invention.

Preferably, the storage stable solution is a solution comprising ethene solubilized in a reactivity reduced liquid, preferably a purified liquid, and most desirably a deionised liquid such as are known in the art or otherwise defined herein.

In a further aspect of the present invention lies in a tonic solution comprising ethene solubilized in a reactivity reduced liquid.

The applicant has surprisingly found that undesirable chemical reactions associated with decay of ethene in a liquid, and the tendency for ethene to undergo reactions over time in a liquid, may be substantially limited by solubilizing ethene in a reactivity reduced liquid. Preferably, the reactivity reduced liquid is a purified liquid, and most desirably is a deionised liquid.

A reactivity reduced liquid may be produced in a number of ways. It is well recognised that ionic mobility is inversely proportional to the viscosity of a medium (Waldren's Law). It follows that the chemical and/or storage stability of a solubilized ethene solution can be further enhanced by increasing its viscosity. The applicant has surprisingly found that this law may be usefully applied to liquids for use in producing ethene solutions by the inclusion of substances in the liquids to increase the liquids viscosity. Any suitable substance capable of increasing the liquids viscosity may suffice. Sugar is particularly preferred by reason of flavour and its non-electrolytic property, that is, sugar does not dissociate into ions that may react with ethene or other ions in solution.

Any suitable sugar may be used. However, glucose and/or sucrose are preferred. The amount of sugar per litre of liquid solution may be adjusted to suit any particular circumstance in respect of desired flavour and/or inhibition of ionic reaction required in the liquid. Sugars and in particular refined sucrose, on average may contain impurities and ionic material in a ratio 1:1000 of sugar by weight so therefore should preferably be further purified and/or deionised prior to use in the storage stable solution. It is also preferred that the liquid so prepared be sterilized, according to methods known in the art, prior to addition of ethene. A suitable sterilisation technique is UV radiation.

The relative viscosity of a cane sugar containing ethene solution as compared to water, may be conveniently determined by a viscometer or alternately gauged by determining its specific gravity. At 20 degrees celsius, water=SG 0.998234. Preferred is a solubilized ethene solution of between SG 1.00250 and SG 1.08462. More preferred is a solubilized ethene solution of SG 1.03985.

In an alternate embodiment, the reactivity reduced liquid may be produced by increasing the purification of the liquid. Therefore, in a preferred embodiment, the reactivity reduced liquid is a purified liquid.

A purified liquid may be produced by subjecting a selected liquid to purification processes known in the art such as filtration, centrifugation, sedimentation, flocculation, distillation, degassing and/or deionization by anion and cation exchange. Pre-prepared liquids with a relatively high level of purity (or relatively low level of impurities) suitable for use in producing a storage stable solution of the invention may be used.

Ionisation may be measured by the conductivity of the liquid., Liquids preferred for use will generally have a conductivity, of less than 50 and preferably less than 15 and most preferably 3 micromhos/cm or less. The applicant has found that the reactivity of ethene upon addition to the liquid reduces proportionately with the reduction of the liquids conductivity. Most liquids contain carbonic acid which affect determination of ionisation levels. For accuracy of results, it is therefore desirable to remove any carbonic acid present in the liquid before determining ionisation levels.

In a further embodiment, the reactivity reduced liquid used in the invention is a deionised liquid. Deionisation may be effected by passing the liquid through cation and anion exchange mediums such as are known in the art. Ion exchange resins are presently preferred for use.

In one embodiment a usefully deionized liquid is one where the ion content is reduced below the weight in milligrams of the level of ethene to be added to the liquid on a mg per mg basis.

Liquids suitable for use in the production of the storage stable solution of the present invention are many and varied. For example, soft drinks, juice, cordials, wine or water could be used.

As noted above, the liquids are generally purified and/or deionised prior to use in the preparation of the storage stable solution of the invention. Suitable pre-prepared liquids may also be employed.

It is also preferred that the liquid be sterilized, according to methods known in the art, prior to the addition of ethene. A suitable sterilization technique is UV radiation.

The liquid presently preferred for use is water, and most preferably purified water. Desirably, the conductivity of the water is reduced from a conductivity of 148 micromhos/cm to 3 micromhos/cm or less. A reduction in conductivity of this magnitude provides a liquid which is very substantially reactivity reduced. The applicant has found that little if any chemical reaction occurs upon the addition of ethene to such deionized water.

In terms of deionized water such water should generally have an ion content of, or less than 1260 milligrams per litre (mg/L), more preferably less than 500 mg/L and most preferably less than 14 mg/L at 10 degrees celsius at atmospheric pressure.

The gases may be entrained in the liquid using procedures well known in the art. Particularly suitable is entrainment using a proprietary gas to liquid saturator such as are commonly used for the production of carbonated soft drinks but any suitable gas to liquid saturating device is envisaged for use. A carbon dioxide/ethene gas mix may even be frozen then introduced into a liquid to infuse into solution without resort to the use of a gas to liquid saturating device.

For entrainment, ethene is preferably compounded with another gas or gases to provide a gaseous compound more soluble than ethene but less soluble than the admixture gas or gases. A suitable admixture gas to provide the compound is preferably carbon dioxide in a ratio of 1:1 or 2:1 vol/vol to ethene. However, any compound formulation suitable for the technical purposes of the invention and applications for the tonic solution may be used.

The applicant has found that when gases such as ethene and carbon dioxide exit a gas mixing/regulating valve into a tube designed to carry the gas mixture to or into a liquid, the gases tend to separate out of the mixture making it more difficult to get the compound to solubilise. To reduce this problem the applicant has adopted the use of a baffle device in the gas line to ensure adequate mixing.

The baffle should be placed in the gas line as close as practicable to the point where the compound is to be solubilized. Any conventional baffles suitable for this purpose may be used. A chamber filled with glass beads is particularly suitable.

The applicant has also found that ethene containing solutions for human oral consumption may be distasteful to consumers to the point of being emetic, thereby defeating the intended utility of the solution.

In order to overcome this problem, the applicant has found that the inclusion of one or more flavouring and/or colouring agent(s) in the ethene containing solution can significantly increase its potability. The flavouring and/or colouring agent is preferably admixed with the selected suitable liquid prior to purifying and/or deionising the liquid and adding ethene.

Any known flavouring agents suitable for this purpose may be employed. Preferred flavouring agents include for example, sugar(s), mint, or lemon.

In another embodiment, the storage stable solution may further comprise a dietary supplement. Many such dietary supplements are known. They include for example, vitamins, minerals, fatty acid(s) (oils), biotin, selenium and the like.

Vitamin C is particularly preferred. Apart from providing a useful dietary supplement, it may scavenge the undesirable reactant, oxygen, from the ethene/liquid solution. Vitamin C may also enhance the bio-availability of ethene within the consumer.

In a further embodiment, the storage stable solution may also comprise one or more additional active agents. These other agents may act to enhance the effect of the storage stable solution in an additive or synergistic manner. They may comprise compounds or substances that provide a useful metabolic, physiological, prophylactic and/or therapeutic effect. These may include anti-infective agents, other antimicrobially effective agents, pain relief preparations and organic extracts. Examples of these active agents include quinine, aspirin, caffeine, glucose or other sugars, interferons and tinctures (e.g. Echinacea).

The storage stable solution of the present invention produces a useful metabolic effect in a host animal to which it is administered. The useful metabolic effect may comprise immune system enhancement, inhibition of, or reduction in levels of, undesirable microorganisms, or other prophylactic or therapeutic effects such as lowering of body temperature or lifting of depression. All of these useful effects may ultimately improve metabolic function in the host.

By way of example, one metabolic effect which may be observed using the methods of the present invention, and which may provide for a therapeutic effect in a host with a high fever, is a lowering of body temperature of the host. This may be particularly important in hosts running high fevers. Another therapeutic effect which may be observed is the amelioration of lymphatic node swelling. Amelioration of the symptoms of wart virus and chicken pox infections have also been observed using the methods of the present invention. Anecdotal evidence from HIV and Hepatitis C trialists also suggests utility of ethene or ethene containing solutions of the invention in alleviating depression.

In one general aspect, the present invention therefore provides a method of improving metabolic function in a host which method involves administering to the host an effective amount of the storage stable solution of the invention.

Because of the high reactivity of ethene, it is also contemplated that the solutions of the invention may find utility as detoxicators. However, the ethene containing solution is primarily intended for use as a tonic for human consumption.

One characteristic the storage stable solution exhibits is a direct antimicrobial effect on many micro-organisms. Therefore, in one embodiment the solution is a direct acting antimicrobial agent. The utility of ethene containing liquids as direct acting antimicrobial agents is generally demonstrated in WO 95/17214 which is incorporated herein by reference. It may therefore be used as a sterilizing agent or surfactant for any of the purposes as set out in WO 95/17214.

Hence, in a further aspect the invention provides a method of prophylaxis and/or therapy for the treatment of diseases or infections in a host by exhibiting a direct antimicrobial effect, and which method comprises administering to the host an effective amount of a storage stable solution of the invention.

Micro-organisms which have shown themselves susceptible to direct antimicrobial action by the storage stable solution of the invention include viruses such as rhinoviruses, bacteria such as motile forms of bacillus and coccus, and fungi such as Candida albicans.

The storage stable solution is generally contemplated for oral consumption. Once consumed, the ethene from the solution may diffuse into the bloodstream via the intestinal tract. This may in turn stimulate the production of ethene from food material within the tract, or may stimulate bodily production of ethene.

It is also contemplated that the solution be formulated for administration by non-oral means such as intravenous administration. It is noted that ethene is more readily soluble in ethyl alcohol. Non-oral administration may be particularly suitable for patients who are unable to consume the solution.

Such a non-oral solution may comprise for example, ethene solubilized in deionised water and ethyl alcohol but not carbon dioxide. A suitable formulation may be 950 ml deionised water, plus 50 ml ethyl alcohol, in total containing 150 ml vol/vol ethene. Other suitable formulations may be readily produced by the art-skilled worker.

The storage stable solution may also be used in methods of therapy by itself or in combination and/or conjunction with other active agents as noted above. Sequential administration of the storage stable or tonic solution and other active agent(s) are specifically contemplated.

The solution will be administered in an amount sufficient to induce the desired metabolic, prophylactic or therapeutic effect. In this application all measures are calculated for average adult weights of 70 kilograms. A particularly suitable amount of solution is an amount which provides for 300 millilitres of ethene gas to be absorbed into the host per dose per day. Lower amounts of, for example, 25 millilitres per day may also be employed. Daily dosage may be determined according to factors such as host weight and the clinical efficacy observable from any given dose amount.

The daily amount of solution may preferably be administered once a day. However, administration may be cumulative via multiple doses over the course of a day or even one dose over days. For example, for Glandular fever infection, a daily dose of 1×300 millilitres of ethene gas given over two days may suffice.

The period of time over which the solution is administered (i.e. the number of days) will be dependent on the nature of the effect to be achieved, or infection or disease against which prophylaxis and/or therapy is desired. Intermittent dosing regimes may also be employed, for example day on day off, week on week off, or month on month off.

In any event, the dosage amount and treatment regime will be formulated to provide any desired clinical efficacy. Variable dosage amounts and treatment regimes are therefore envisaged.

As indicated above, ethene also has applications in: methods of therapy and/or prophylaxis for the treatment of diseases or infections in a host, or improving metabolic function, other than through exerting a direct antimicrobial effect; methods of priming and/or causing a host to mount a protective response, more particularly a protective immune response against disease or infective micro-organisms; methods of administering ethene to a host wherein the ethene provides an indirect sterilizing or micro-organism inhibiting effect, such effect being prophylactic and/or therapeutic and such effect being caused by host systemic factors, for example, T-lymphocytes or leukocytes, potentiated in the host by the administration of ethene; and methods of therapy and/or prophylaxis against microbial infection in a host which comprises the steps of:

(a) administering an effective amount of ethene to said host to potentiated and/or prime the immune system of the host to generate a host protective immune response against said microbial infection; and (b) administering an amount of an active agent which has a direct antimicrobial effect sufficient to sterilize or at least inhibit the micro-organism.

The essential step of these latter aspects of the applicants invention is the administration of ethene to a host in need of metabolic, prophylactic or therapeutic treatment. To facilitate this, the ethene may be administered in any convenient form. Most conveniently, the ethene is administered in the form of a composition in which ethene is solubilized in any suitable liquid such as water. A composition containing ethene in water, as taught in WO 95/17214, may be suitable. A storage stable solution of the present invention is particularly acceptable by reason of enhanced stability and/or purity in comparison to a solution comprising a non-purified liquid.

It will also be appreciated that the ethene could be administered directly to the host via inhalation, preferably in admixture with another gas. Desirably, a quantity of 5.6% or less of ethene in air may be used but the air may be replaced with other suitable gases or gas such as oxygen. Any convenient route of administration may be used, aspiration via the lungs being one example. Absorption into the recipient may be calculated on the basis that the average maximal inhalation absorption rate for an adult human is 25 litres of ethene gas per hour and that the ventilation rate of the adult lungs is on average 450 litres per hour. Dosage rates may therefore be readily calculated on a time/ethene concentration/ventilation rate basis. Generally, aspiration of ethene is a less preferred method of administration.

The ethene will be administered in an amount sufficient to induce the desired metabolic, protective or immune response. As noted above, in this application, all measures are calculated for average adult weights of 70 kilograms. A particularly suitable amount is 300 millilitres of gas absorbed into the host per day, but lower amounts for example 25 millilitres per day, may be employed. Daily dosage will need determination according to factors such as host weight and the clinical efficacy observable from any given dose amount.

The daily amount of ethene may be administered/ once daily and this is in fact preferred when a composition as described in WO 95/17214 or a solution of the present invention is used. However, the administration may be cumulative via multiple doses over the course of a day or even one dose over days.

The period of time over which the ethene is administered (i.e. the number of days) will be dependent on the result to be achieved and/or the nature of the infection or disease against which the prophylaxis and/or therapy is desired. With HIV/AIDS for example, a treatment regimen may suitably consist of 42 days at 300 millilitres daily and may or may not be followed by a period of abstinence, for example 28 days, followed by a further ethene treatment regimen. In some circumstances, ethene may even be required to be administered daily for an indefinite period of time.

As noted above for the direct acting methods, the applicant envisages a dosage amount and a treatment regimen will be formulated to provide any given clinical efficacy that may be desirable. Variable dosage amounts and treatment regimens are envisaged.

The ethene can be administered as the sole active agent or in combination and/or conjunction with other active agents. For example, in the treatment of HIV/ADS, the administration of ethene in conjunction and/or in combination with one or more agents, for example AZT having direct anti-viral activity may be synergistic and may provide a therapeutic efficacy the sum total of which exceeds the combined sums of efficacy of the individual agents when used in monotherapy. In these applications, the ethene may act to enhance the effect of the agent having the direct antimicrobial activity. This enhanced effect may not only be increased antimicrobial efficacy but may include an ability to reduce toxicity to the host of any given active (including toxic) agent, for example AZT.

The ability of reactive ethene to reduce the toxicity in a host of another active agent may arise for example, by ethenes ability to trans-methylate methyl groups. Such a methyl group is found in the active agent AZT. Toxicity of methyl groups may be reduced or eliminated via a molecular chain lengthening action such as ethene may provide.

As is described in more detail in the experimental section below, a particular therapy using two active agents, ethene and AZT, whereby ethene was administered for 6 weeks followed by AZT for 8 weeks, was found to provide a dramatic recovery in CD4 T-Cell count being a recovery over the period of time, that was well above (according to published data) what would be expected with AZT monotherapy.

For both direct and indirect methods of prophylaxis and therapy in this invention it is anticipated that the ethene, or ethene containing solutions may have greater efficacy if applied from the onset of infection when the microorganism load is low. This may be particularly the case for HIV infection where the viral load is relatively low in the early stages, compared with terminal stages where the viral load is very high and the immune system deficient.

The prophylactic and/or therapeutic effect of ethene, in respect of the indirect methods of the invention, in the applicants belief, arises via the ability of ethene to induce in the host, the activation of, or an increased production of systemic factors involved in mounting an immune response, particularly those factors involved in mounting a humoral immune response. An example of a cell population found to be increased is that of CD4 T-lymphocytes in humans. Other factors include leukocytes such as basophils and neutrophils, phagocytes and enzymes such as alanine-aminotransferase.

It is the applicant's theory that the increased production of immune cells, or their activation, is part of a general effect ethene has on the host in boosting/promoting amino acid/protein synthesis (including enzymes such as alanine amino transferase). However, the applicant is by no means bound by this theory.

It is further proposed that microorganisms may be inhibited by the ethene reacting with ATP to deny that ATP to the microorganism thereby interfering with replication. Again, the applicant is however in no way bound by this theory.

The invention will now be illustrated by reference to the following non-limiting examples.

Non-Limited Examples of Utility of the Invention

Three HIV+ volunteers codenamed Tom, Ian and John, secretly trialed a composition comprising solubilized ethene. The CD4 T-lymphocyte count was used as a marker, any increase in cell count or slowing of rate of loss being evidential of utility.

The composition was prepared using sterile filtered and dechlorinated water which was then chilled to 3° C. and passed through a carbonator, containing ethene and an admixture of carbon dioxide, to effect an absorption of ethene into the liquid of about 40% ethene gas by volume to liquid at ordinary atmospheric pressure. This composition was then packaged into 745 millilitre bottles giving 300 miuilitres of ethene per bottle vol/vol liquid.

In these Examples, cell counts are given as cells per microlitre of blood, often expressed as $mm^3$.

Example 1

Trialist "Tom" consumed one bottle daily for four weeks during which time an apparent (3.6%) slow-down in CD4 cell rate of decline was observed. Within 18 hours of therapy commencement, the continuous diarrhoea he suffered ceased and the oral Candida albicans infection he had disappeared. During the therapy he gained 2 kilograms in weight Six weeks later he undertook another two week course of consumption. During the six week interval he fell ill. During the final two week trial, his CD4 cell count rose by 20 per $mm^3$ and he gained a further 2 kilograms in weight. This recovery indicated a complete reversal of CD4 cell loss into a substantial gain. During a course of AZT (Zidovudine) of 500 milligrams daily, immediately after the final two weeks consumption of the ethene composition, his CD4 cell count rose by a count of 210 over eight weeks, being an increase of some 150 cells over and above maximum recovery rates generally observable with AZT monotherapy. This CD4 T-Cell recovery exceeded by 23.5% a later AZT/3TC combination therapy he undertook.

Example 2

Trialist "Ian" consumed one bottle daily for an unbroken six week period. During this time there was no decline in his CD4 cell count which is indicative of loss stabilisation. In the eight week period following, his CD4 cell count increased by a count of 20.

Ian maintained certain life-style practices, for example smoking, that may have impaired his recovery rate, however the utility of the invention is again demonstrated by this result Example 3

Trialist "John" also consumed one bottle daily for six weeks. During this period his CD4 cell count declined from 145 to 70. His average decline in CD4 cell count for the prior 11 weeks inclusive of the 6 week therapy, was 10.9 cells per week (cpw). During this period an amelioration of his acne symptoms was observed. Continuing the daily dosage regimen, over the next four weeks, by the end of week ten his CD4 cell count had risen to 120, a gain of 12.5 cpw and a substantial amelioration of lymphatic node swelling was apparent during medical examination (lymphatic node swelling is a symptom of HIV infection which becomes more evident as the disease progresses). Continuing the regimen, by week 17 week his CD4 cell count had declined to 80, a decline of 5.7 cpw. By week 26 his CD4 cell count had declined to 40, a decline of 4.4 CD4 cpw. By week 31, his CD4 cell count had stabilised at 40, a zero loss of cpw and he had gained 2 kilograms in weight. During the subsequent 6 weeks of ethene therapy, he gained a further 3 kilograms in weight.

As of May 1, 1997, this trialist had been on daily ethene therapy for 20 months in combination with an anti-bacterial. During this period he has had no infections, apart from his incumbent HIV, whatsoever. He had no AIDS related events, gained weight and maintained good health. It can be seen that his rate of loss of CD4 cells substantially declined during the therapy and indeed, the cell count substantially increased at one point.

FIG. 1 graphs the progress of the trialists and shows the immune response in respect of CD4 T-lymphocyte recovery and/or a decline in loss rate as examples of the utility of the invention.

The therapies (if any) undertaken by the trialists are shown as:

EH=Solubilised Ethene, AZT=Zidovudine, 3TC= Lamivudine

Example 4

As a further example, a trial was undertaken on a Hepatitis C (genotype unknown) sufferer. A daily dose of 230 millilitres of ethene gas was solubilized into 745 millilitres of purified water without an admixture of carbon dioxide.

The infection marker used was the Alanine-aminotransferase (ALT) count. ALT is an enzyme normally present in serum and body tissues, especially the liver. It is released into serum as a result of tissue damage and is therefore a good marker of hepatic cell damage (infection level) in Hepatitis infection.

During the first 18 days therapy, an amelioration of infection symptoms was observed. Bowel motions restored to normal texture. Urine restored to normal colour, lethargy decreased and liver tissue function improved. The trialist also reported that he experienced a significant lifting of his depression. By the end of week 4, the ALT count declined from 242 to 218 u/l indicating a lessening of infection. From week 4 to the end of week 6, the ALT count rose from 218 to 303 u/l. Similar percentage increases in ALT count may be observed in non-infected persons administered ethene at the same or a similar dose ratio. The ethene (or disease) stimulated synthesis of ALT appears to be an intermediate systemic immune response. Tissues and cells subjected to damage, as in pathogenic attack, markedly increase ethene production. From week 6 to the end of week 14 there was a substantial decline in ALT count from 303 to 93 u/l. In weeks 14 through 16 the ALT decline flattened out, declining to 89 u/l.

Figure 2:
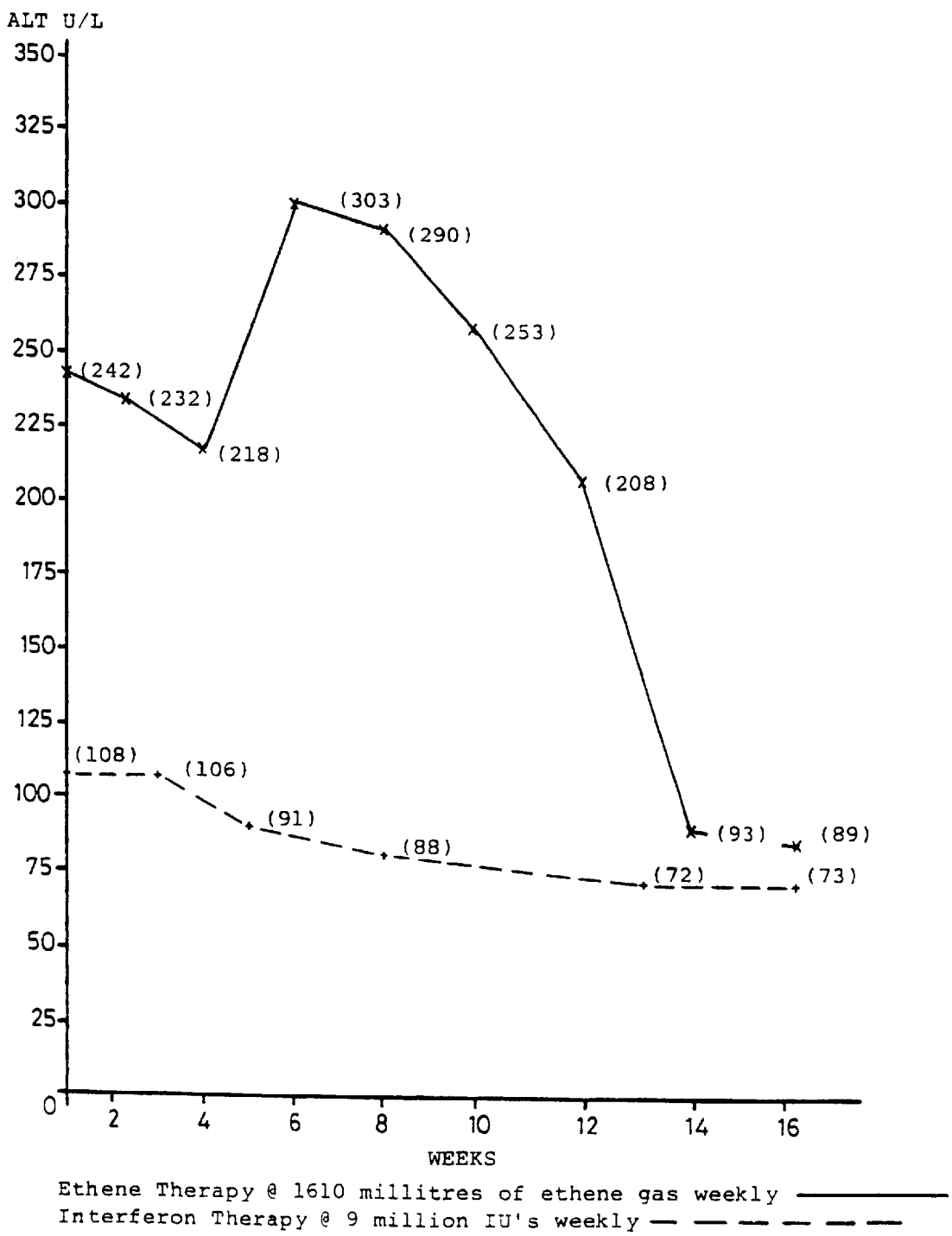
FIG. 2 illustrates the comparative effects of the administration of ethene and interferon on an individual infected with Hepatitis C.

FIG. 2 charts the progress of the therapy in comparison to an earlier interferon therapy (9 million IU weekly) undertaken by the trialist. In terms of infection marker reduction, ethene in this example reduced the ALT count by 153 u/l compared to interferons 35 u/l over the same 16 week trial period. In this example, ethene provided an anti-Hepatitis C efficacy 337% better than the interferon therapy. This example further demonstrates the utility of the invention.

Example 5

In an effort to determine what, if any, effect the invention would have on white blood cells (the immune cells) a trialist undertook a four day course of the tonic comprising 300 millilitres of ethene solubilized into a purified liquid, on a daily basis. Blood samples were taken immediately before and immediately after the course. Five blood samples were taken over a period of six months to determine the volunteers ordinary average (O.A.) cell count and the normal adult human range is also shown as cells per microlitre

| O.A. | Start | Finish | Gain | Normal | Range |
|---|---|---|---|---|---|
| (1) 3,580 | 4,300 | 10,100 | 135% | 4,000> | 11,000 |
| (2) 1,940 | 2,200 | 8,800 | 300% | 2,500> | 7,500 |
| (3) 60 | 100 | 800 | 700% | 15> | 100 |
| (4) 1,040 | 1,100 | 0 | −100% | 900> | 3,600 |
| (5) 420 | 700 | 300 | −57% | 100> | 800 |
| (6) 100 | 200 | 200 | 0% | 100> | 500 |

(1) White Blood Cells (2) Neutrophils (3) Basophils
(4) Lymphocytes (5) Monocytes (6) Eosinophils It can be seen that there was a dramatic increase in quantity/activation of immune cell lines (1), (2) and (3) and a dramatic increase in activity of immune cell lines (4) and (5), thereby demonstrating the immunogenic role of ethene in human metabolism as further shown in Examples 1, 2, 3 and 4.

In this example a total average percentage increase in quantity and/or activation of 258.4% is seen in white blood cell lines 1, 2, 3, 4 and 5, thereby providing evidence of the utility of the invention in providing a useful metabolic effect by stimulating a protective response in vivo.

Example 6

This example demonstrates the observable effect of consumption of the tonic in lowering body temperature. A volunteer fitted with a LCD rectal thermometer calibrated in 10ths of a degree celsius steps, consumed over 5 minutes, 745 millilitres of the tonic containing 300 millilitres of solubilized ethene gas. The volunteers temperature was stable at 37.2° C. for the 5 minutes prior to the test beginning and the room was maintained at 25° C. The following body temperature changes were observed:

| Elapsed Minutes | Temperature |
|---|---|
| Start | 37.2 |
| 3 | 37.1 |
| 12 | 36.9 |
| 24 | 37.1 |
| 35 | 37.2 |
| At this point a few steps were taken to restore circulation | |
| 37 | 36.8 |
| 40 | 37.1 |
| 45 | 37.2 |

The temperature stabilised back to 37.2 and the volunteer consumed a further 300 millilitres of solubilized ethene gas of the tonic.

| | |
|---|---|
| Start | 37.2 |
| 1 | 37.1 |
| 43 an abrupt lowering to | 36.7 |
| 45 | 36.9 |
| 55 an abrupt raising to | 37.1 |
| 140 | 37.2 |

While it took only 45 minutes for body temperatures to restore after the first dose, it took 140 minutes, 211% longer, to restore to 37.2° C. after the second dose. This example demonstrates a reaction between ethene and the energy (heat) releasing molecule Adenosine tri-phosphate (ATP). This phenomenon has been observed in actively fermenting yeast.

Example 7

This example demonstrates that removal of impurities including ions from a suitable liquid (in this example potable mains town supply water), provides a liquid that upon the addition of ethene, remains more chemically and storage stable compared to the same or a similar solution prepared using the impure mains water.

In this example, high purity mains water supply water is used (the raw water) having a conductivity of 148 micromhos per centimetre at 20 degrees celsius, a pH of 7.2 and a pH of 7.6 after carbon dioxide removal by boiling. The conductivity indicates a high ion content whilst the pH indicates an excess of hydroxyl ions.

2×1 litre flasks containing 500 millilitres of the water (1×boiled and 1×not boiled) and 500 millilitres of technical grade ethene gas in each were vigorously shaken to solubilise the ethene and then the pH immediately determined. A rise of 0.1 pH was observed in each.

A further flask containing 500 millilitres of the water which had been deionised and impurities removed by a single pass distillation, giving a pH of 7.0 and a conductivity of 0.1+ or −0.1 micromhos per centimetre, was solubilized in the same manner with 500 millilitres of ethene. An immediate reading of the pH showed no change. This indicates a reactivity of ethene in ionised water containing impurities that is not apparent in deionised water. After some 5 minutes, it was observed that the pH of the non-deionised samples returned to their respective prior ethene addition pH, indicating a secondary reaction had also occurred.

Example 8

380 litres of water direct form the mains supply was boiled to remove the impurity oxygen and carbonic acid. The resultant pH was 7.6. 380 litres of ethene gas and 760 litres of carbon dioxide gas was solubilized into the water using a proprietary "CEMCO" gas to liquid saturator and then the resultant solution was bottled into crown sealed bottles using an automatic filler/capper.

On bottling (day 1), the solutions pH was 4.2 due to the formation of carbonic acid via the added carbon dioxide and the presence of a reactant calcium hydroxide in the liquid. On day 6, the pH had dropped to its ionic equilibrium and stabilised at 4.1. These reactions did not involve ethene. On day 12, the pH had risen to 4.2, and on day 40, the pH had risen to 4.3. These rises in pH show a chemical instability in the solution and a continuing production of hydroxyl ions. After 9 months storage, the pH had risen to 4.9. Given the pH buffering effect of the entrained carbonic acid, the overall rise in pH denotes the major chemical and storage instability of the solution. A portion of the solution was then boiled to remove the carbonic acid and the pH determined. The pH reading was 8.7 as compared to its original carbonic acid free pH of 7.6. This overall rise of pH 1.1 indicates a large increase of hydroxyl ions in the solution during the course of storage due to the chemical instability of the solution. It was found that in similar solutions made without the inclusion of ethene as an ion acceptor, the pH remained very stable, rising at most by pH 0.1. It was found that if a suitable liquid, in this instance water, was processed to remove impurities particularly ions before being used to produce an ethene/liquid solution, that the solution so produced would remain very pH stable, rising at most over 6 months storage by pH 0.1, thus providing a more chemically and storage stable solution.

Example 9

In this example it is shown how a suitable liquid, water, may be processed to remove impurities. The water is passed through a sand filter containing suitably graded sand, to remove suspended material such as plant matter etc., then passed through a suitably sized and graded activated carbon filter to remove reactants such as chlorine. The efficacy of the carbon filter should be regularly monitored with suitable reagents to ensure complete chlorine removal from the water. Depending on the type and level of solutes in the water, sand and activated carbon filtering may deionise the water by about pH 1.1. If any additives such as flavouring agents are added, they may be added at this stage.

The water is then passed through a sheet or other suitable filter or filters which may or may not be positively charged. Preferably a sequence of filters is used whereby the nominal retention rating starts at 8 microns and finishes at 0.2 microns. On exiting these filters, the water is then passed through a mixed resin ion exchange bed to totally, insofar as is possible, remove any remaining excess ions. Water exiting the ion exchange bed should be of neutral pH, that is, pH 7.0. The conductivity of the water should then be less than 1 micromho per centimetre. The purity of the water for any given conductivity will need to be determined by laboratory analysis. For example, carbonic acid break-through may raise the conductivity of the water but appears to have little if any reactant role in ethene solutions. The water is preferably then filtered again starting from 1.2 down to 0.2 microns.

The water is then preferably degassed to remove reactants such as oxygen and air for example. For this, on a small scale for example, the water is transferred into a suitably sized cylindrical conical stainless steel tank fitted with a stainless steel sintered element in its base. The tank and its contents are pressurised with nitrogen gas to 2 atmospheres. Nitrogen gas is introduced into the liquid via the sintered element, to pass through the liquid as fine bubbles which deoxygenate the liquid, then are vented to atmosphere via a pressure relief valve. The vented gas may be recovered, purified and reused. Typically, such a method can reduce oxygen levels to 0.1 parts per million. The liquid is then preferably sterilized with UV radiation. After this, the water is ready for the addition of ethene and/or other gases.

It was found that solutions of the invention produced by other than this process may contain microscopic sites upon which ethene may react and forming for example, unsightly polymeric flocs, thereby seriously reducing the solutions stability and industrial acceptability.

Using this or similar methods to produce purified and/or deionised liquids results in solutions which when stored for 12 months have shown no statistically significant change in pH over the storage period, indicating excellent chemical and storage stability compared to solutions produced not using the method.

INDUSTRIAL APPLICABILITY

The storage stable solutions of the invention may find wide application in the inhibition or elimination of microorganisms in liquids. More specifically, the invention provides tonic solutions for human use. The use may be in methods of therapy and/or prophylaxis as a directly active antimicrobial agent in the human body. Other indirect methods of therapy and/or prophylaxis, or immune system enhancement involving the administration of ethene are also provided for.

It is to be understood that the scope of the invention is not restricted to the above examples and that numerous variations and modifications may be made to those examples without departing from the scope of the invention as set out in this specification.

What is claimed is:

1. A method for improving metabolic function in a host which comprises administering to the host an effective amount of storage stable ethene.

2. The method as claimed in claim 1, wherein one or more other active agents or dietary supplements are separately or co-administered to the host.

3. The method as claimed in claim 1, wherein the improvement in metabolic function is an enhancement of the immune system.

4. The method as claimed in claim 1, wherein the improvement in metabolic function comprises one or more of the following: a lowering of body temperature; lifting of depression; and a reduction in lymphatic node swelling.

5. A method of priming or causing a host to mount a protective response against a disease or an infective microorganism which comprises administering to the host an effective amount of ethene.

6. The method as claimed in claim 5, wherein the protective response is a protective immune response.

7. The method as claimed in claim 5, wherein the protective response is a humoral immune response.

8. The method as claimed in claim 5, wherein the protective response is an increase in enzyme synthesis.

9. The method as claimed in claim 5, which further comprises separately administering or co-administering to the subject one or more other active agents or dietary supplements.

10. The method as claimed in claim 5, wherein the ethene is solubilized in a liquid.

11. The method as claimed in claim 10, wherein the ethene is in a storage stable solution.

12. A method of treating HIV, hepatitis, glandular fever, or herpes simplex in a subject which comprises administering to the subject an effective amount of storage stable ethene.

13. A method of treating cancer in a subject which comprises administering to the subject an effective amount of storage stable ethene.

\* \* \* \* \*